United States Patent [19]

Sawyer et al.

[11] Patent Number: 5,472,942
[45] Date of Patent: Dec. 5, 1995

[54] ANTI-THROMBINS

[75] Inventors: Roy Sawyer; Christopher Powell-Jones, both of Dyfed; Anthony Atkinson; Asgar Electricwala, both of Salisbury, all of United Kingdom

[73] Assignee: Biopharm (UK) Limited, Hendy, United Kingdom

[21] Appl. No.: 721,536

[22] PCT Filed: Nov. 13, 1989

[86] PCT No.: PCT/GB89/01345

§ 371 Date: Jul. 10, 1991

§ 102(e) Date: Jul. 10, 1991

[87] PCT Pub. No.: WO90/05143

PCT Pub. Date: May 17, 1990

[30] Foreign Application Priority Data

Nov. 11, 1988 [GB] United Kingdom ............... 8826428

[51] Int. Cl.$^6$ ............................ C07K 14/00; A61K 38/16
[52] U.S. Cl. ............................................. 514/12; 530/324
[58] Field of Search ................................. 514/12; 530/324

[56] References Cited

U.S. PATENT DOCUMENTS 4,390,630  6/1983  Sawyer et al. ..................... 435/226
4,820,516  4/1989  Sawyer et al. ..................... 424/94.62
5,114,922  5/1992  Maschler et al. ..................... 514/12
5,139,944  8/1992  Sawyer et al. ..................... 435/226

Primary Examiner—Jill Warden
Assistant Examiner—Carol Salata
Attorney, Agent, or Firm—Darby & Darby

[57] ABSTRACT

A polypeptide derived from leeches of the species *Hirudinaria manillensis* has the following amino acid sequence:

```
                5              10              15
Xaa Xaa Tyr Thr Asp Cys Thr Glu Ser Gly Gln Asn Tyr Cys Leu 20              25              30
Cys Val Gly Ser Asn Val Cys Gly Glu Gly Asp Asn Cys Asn D 35              40              45
Gln Leu Ser Ser Ser Gly Asn Gln Cys Val E Gly Glu Gly Thr 50              55              60
Pro F Pro Gln Ser Gln Thr Glu Gly Asp Phe Glu Glu Ile Pro

65
Asp Glu Xaa Ile Lys
``` wherein Xaa indicates any amino acid residue; D indicates Cys or Pro; E indicates Glu, Asp or His; F indicates Asp, Lys or Trp; or a pharmaceutically acceptable salt, derivative or bioprecursor thereof. The polypeptide, and fragments thereof, is a specific anti-thrombin useful as a medicament.

17 Claims, 6 Drawing Sheets

ANTI-THROMBINS

The present invention is concerned with novel anti-thrombins and, in particular, novel anti-thrombins derived from leech tissue and leech secretions.

Hirudin is a well known and well characterised polypeptide, which is known to be specific for thrombin, and which is obtained as an extract from leeches of the species *Hirudo medicinalis*. The polypeptide has a relatively low molecular weight (ca.7000) and is comprised of 65 amino acids. The sequence of first isoform of hirudin has been determined by Dodt, Muller, Seemuller and Chang ("The complete amino acid sequence of hirudin, a thrombin-specific inhibitor"; FEBS 165 (1984): pp180–184) to be as follows (SEQ ID NO:1):

```
              5                  10
Val Val Tyr Thr Asp Cys Thr Glu Ser Gly Gln Asn Leu Cys 15                 20                  25
Leu Cys Glu Gly Ser Asn Val Cys Gly Gln Gly Asn Lys Cys 30                 35                  40
Ile Leu Gly Ser Asp Gly Glu Lys Asn Gln Cys Val Thr Gly 45                 50                 55
Glu Gly Thr Pro Lys Pro Gln Ser His Asn Asp Gly Asp Phe 60              65
Glu Glu Ile Pro Glu Glu Tyr Leu Gln
```

Two variants of hirudin have also been characterised and the amino acid sequence determined. A first variant, as described by Dodt, Machleidt, Seemuller, Maschler and Fritz ("Isolation and characterisation of hirudin isoinhibitors and sequence analysis of hirudin PA"), Biol. Chem. Hoppe-Seyler, 367 (1986) pp803–811. This variant, designated SEQ ID NO:2, differs from the one described previously, in the following respects:

| | | |
|---|---|---|
| 1. | -Ile- | at position 1 instead of -val- |
| 2. | -thr- | at position 2 instead of -val- |
| 3. | -lys- | at position 24 instead of -gln- |
| 4. | -asn- | at position 33 instead of -asp- |
| 5. | -lys- | at position 35 instead of -glu- |
| 6. | -gly- | at position 36 Instead of -lys- |
| 7. | -asn- | at position 47 instead of -lys- |
| 8. | -glu- | at position 49 instead of -gln- |
| 9. | -asn- | at position 53 instead of -asp- |

A second variant, as described by Harvey, Degryse, Stefani, Schamber et al ("Cloning and expression of a cDNA coding for the anti-coagulant hirudin from the bloodsucking leech, Hirudo medicinalis"), Proc. Nat. Acad. Sci. U.S.A. (1986) pp1084–1088. This is identical to the first-mentioned variant from positions 1 to 32 and then has the following differences from the first-mentioned hirudin: (SEQ ID NO:3):

| | |
|---|---|
| 1. | -gln- at position 33 instead of -asp- |
| 2. | -lys- at position 35 instead of -glu- |
| 3. | -asp- at position 36 instead of -lys- |
| 4. | -gln- at position 53 instead of -asp- |
| 5. | -pro- at position 58 Instead of -glu- |
| 6. | -asp- at position 62 instead of -glu- |
| 7. | -asp- at position 64 instead of -leu- |
| 8. | -glu- at position 65 instead of -gln- |

As indicated above, hirudin has been derived from leeches of the species *Hirudo medicinalis*. *Hirudinaria manillensis* is similar to *Hirudo medicinalis* in that they are both able to feed on amphibian and mammalian blood. However, *Hirudinaria* is evolutionaryly more advanced than *Hirudo medicinalis*. It cannot be predicted with any certainty whether or not an active substance present in the secretions of a first species of leech is likely to be found in a different species, and (if substances of similar activities are found) whether they are likely to have substantially identical amino acid sequences, or markedly different amino acid sequences.

We have now isolated a novel anti-thrombin from *Hirudinaria manillensis*, the anti-thrombin having the following amino acid sequence SEQ ID NO:4:

```
                                              *
              5                   10
Xaa Xaa Tyr Thr Asp Cys Thr Glu Ser Gly Gln Asn Tyr Cys

*                    *    *  *
       15                 20                  25
Leu Cys Val Gly Ser Asn Val Cys Gly Glu Gly Asp Asn Cys

*  *        *  *  *
       30                 35                  40
Asn  D   Gln Leu Ser Ser Ser Gly Asn Gln Cys Val  E   Gly

*   *         *  *  *
           45                 50                55
Glu Gly Thr Pro  F   Pro Gln Ser Gln Thr Glu Gly Asp Phe

*
              60              65
Glu Glu Ile Pro Asp Glu Xaa Ile Lys
```

Comparison with the hirudin sequence indicates approximately 62% homology (that is, about 38% differences), which is a surprisingly substantial difference. There are, in particular, significant differences at the important C-terminus, and the following clear differences:

| |
|---|
| at position 13 (-tyr- instead of -leu-); |
| at position 17 (-val.- instead of -glu-); |
| at position 24 (-glu- instead of -gln-); |
| at position 26 (-asp- instead of -asn-); |
| at position 27 (-asn- instead of -lys-); |
| at position 29 (-asn- instead of -ile-); |
| at position 30 (-pro- or -cys- instead of -leu-); |
| at position 31 (-gln- instead of -gly-); |
| at position 32 (-leu- Instead of -ser-); |
| at position 33 (-ser- instead of -asp-); |
| at position 34 (-ser- instead of -gly-); |
| at position 35 (-ser- instead of -glu-); |
| at position 36 (-gly- instead of -lys-); |
| at position 41 (-glu- or -asp- or -his- instead of -thr-); |
| at position 47 (-asp-, lys or -trp- instead of -pro-); |
| at position 51 (-gln- instead of -his-); |
| at position 52 (-thr- instead of -asn-); |
| at position 53 (-glu- instead of -asp-); |
| at position 61 (-asp- instead of -glu-); |
| at position 64 (-ile- instead of -leu-); and |
| at position 65 (-lys- instead of -gln-).; |

The differences in positions 61 (aspartate instead of glutamate), 64 (iso-leucine instead of leucine), and 65 (lysine instead of glutamine) are believed to be especially important because the sequence 55-64 is thought to be a critical domain for the inhibitory action of hirudin (see in this connection Owen et al, "N-terminal replacement of small peptide anti-coagulants based on hirudin", 1988 J. Med. Chem. 31: pp.1009–1011). The presence of aspartate (-asp-), iso-leucine (-ile-) and lysine (-lys-) in the anti-thrombin according to the invention results in a novel thrombin-inhibiting domain; the sequence 54-65 alone is believed to be novel per se and to have novel anti-thrombin properties. The invention therefore further comprises the small peptide having the amino acid sequence 54-65 as defined above and shown below:

Gly Asp Phe Glu Glu Ile Pro Asp Glu Xaa Ile Lys wherein Xaa represents an amino acid residue; or a pharmaceutically acceptable salt, derivative, or bioprecursor thereof. This sequence is designated SEQ ID NO: 12. When Xaa is Tyr or a sulphated derivative thereof, the polypeptide is designated SEQ ID NO: 13.

The amino acid at position 63 may be tyrosine (tyr), which is typically sulphated. (In contrast, recombinant hirudin is generally not sulphated at this position.)

The leech-derived anti-thrombin according to the invention (and corresponding DNA sequences which can be extrapolated therefrom) is non-homologous with eglin, a known elastase/chymotrypsin inhibitor which is known to be present in the medicinal leech *Hirudo medicinails*, and is described by Seemuller et al in "Eglin: elastase-cathepsin G inhibitor from leeches"; 1981 Meth. Enzymol. 80: pp.804–816.

The anti-thrombin according to the invention is typically isolated either from the tissue of the species *Hirudinaria manillensis* by techniques involving solvent extraction and subsequent fractionation by chromatographic techniques or the like; alternatively, it may be isolated in a similar manner from secretions (such as saliva) of *Hirudinaria manillensis*.

According to a further aspect of the invention, therefore, there is provided an anti-thrombin derived from the tissue or secretions of leeches of the species *Hirudinaria manillensis*. The anti-thrombin is specific in its activity to thrombin.

The present invention further comprises a recombinant or protein-engineered equivalent to the polypeptide of formula indicated above.

Figure 1:
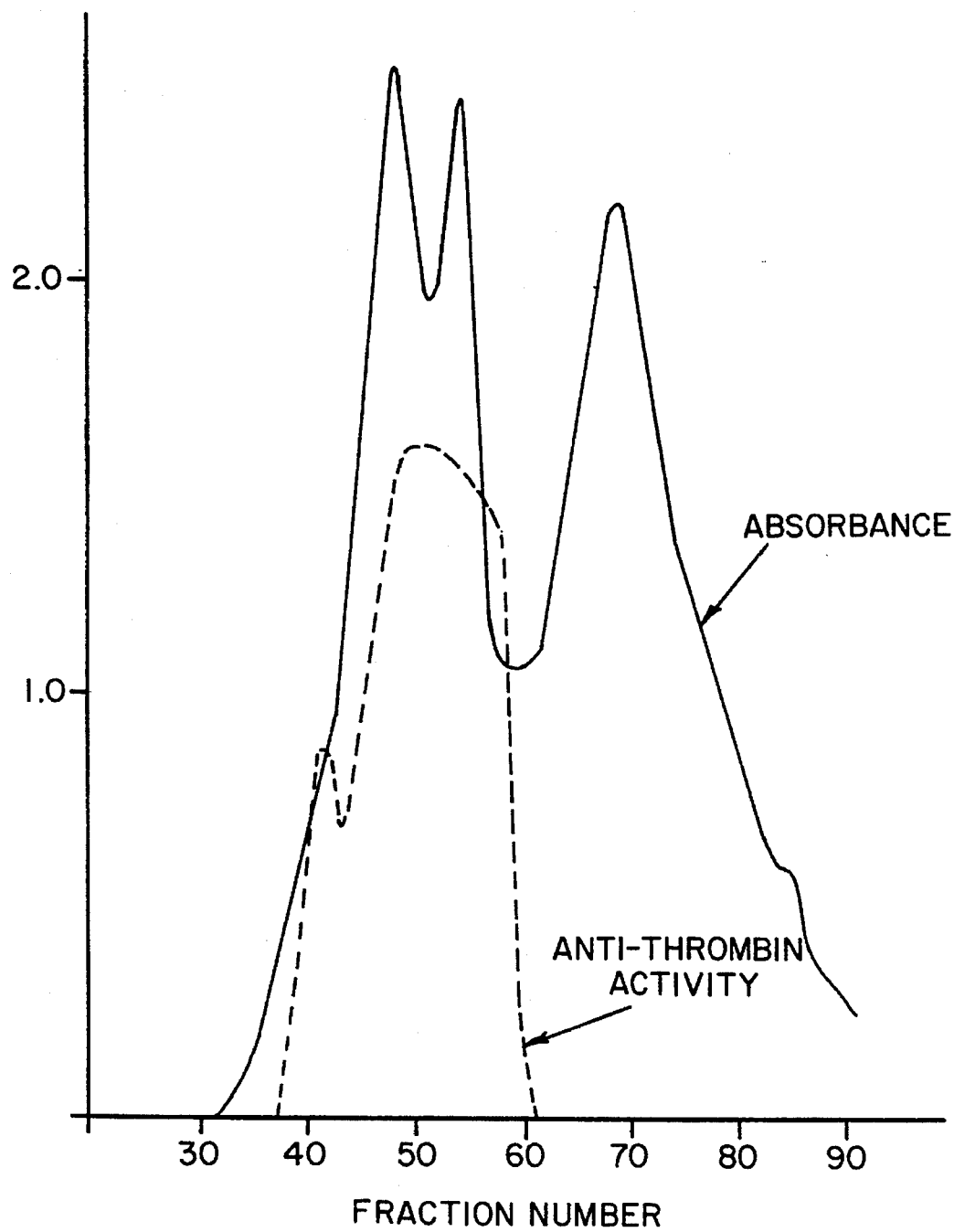
FIG. 1 is a chromatograph of crude leach extract separated of DEAE-A25.

The anti-thrombin according to the invention may be used in a pharmaceutical formulation, together with a pharmaceutically acceptable carrier or excipient therefor. Such a formulation is typically for intravenous administration (in which case the carrier is generally sterile saline or water of acceptable purity). The anti-thrombin according to the invention is suitable for treatment of thromboembolic events, such as the coagulation of blood. In one embodiment of the invention, the anti-thrombin is coadministered with a plasminogen activator, such as tissue plasminogen activator; the anti-thrombin according to the invention has been found to be compatible with the latter.

Exemplary processes for isolation of anti-thrombin according to the invention from leech tissue will now be described in the following detailed Examples.

EXAMPLE 1

Step—Acetone Extraction 600 grams of *Hirudinaria manillensis* leeches were dehydrated in approximately 2 liters of 96% ethanol for 24 hours. The anterior region of the animal was dissected away from the remainder of the body and was further dehydrated in approximately 200 ml 96% ethanol for a further 24 hours.

Dehydrated leech heads were finely chopped into small pieces and a mixture of 40 ml acetone and 60 ml water was added. The mixture was stirred for 30 min at room temperature, spun for 15 minutes at 2,700 rpm and the supernatant decanted.

The pellet was resuspended in a further 100 ml of 40:60 acetone: water mixture, followed by stirring at room temperature for 30 minutes. The mixture was spun at 2,700 rpm for 15 minutes and the supernatant decanted and pooled with the initial supernatant. 80 ml acetone and 20 ml water were added to the pooled supernatant and the pH lowered with glacial acetic acid to 4.4.

The mixture was spun at 2,700 rpm for 15 minutes and the supernatant decanted. The pH of this solution was adjusted to 6.0 using 30% ammonia. The volume was reduced to approximately 30 ml by rotary evaporation at 35° C.

Trichloroacetic acid crystals were added to lower the pH of the solution to 1.8, followed by centrifuging to remove precipitates. The raw anti-thrombin was precipitated from the solution using a 9-fold excess volume of acetone.

The mixture was spun at 2,700 rpm for 15 min and the supernatant discarded. The pellet was resuspended In 50 ml acetone and spun at 2,700 rpm for 10 min; the washings were discarded and the precipitate dried in a vacuum desiccator for one hour. Raw anti-thrombin was reconstituted in 4.0ml of water.

Protein was estimated by absorbance at 280 nm to be 78 mg/ml. The activity was estimated by the prevention of thrombin/fibrinogen clot to be 2400 anti-thrombin units/ml (or about 10,000 anti-thrombin units per 200 grams of chopped heads). The total activity was 9600 anti-thrombin units; and the specific activity was calculated as 30.7 anti-thrombin units/mg protein.

Step 2—Ethanol Extraction

The raw anti-thrombin solution was cooled to 3° C. Six 1.2 ml aliquots of ice cold 96% ethanol were added at 5 minute intervals. The mixture was then left at 3° C. for a further 10 minutes and was then centrifuged at 2,400 rpm for 10 minutes; the supernatant was decanted and retained.

The pellet was resuspended in 4 ml ice cold distilled water, mixed with 7.2 ml ice cold 96% ethanol. This was allowed to stand at 3° C. for 30 minutes and then centrifuged at 2,400 rpm for 10 minutes. The supernatant was decanted off and pooled with the initial supernatant.

The pellet was resuspended in a mixture of 4 ml ice cold 96% ethanol and left to stand for 30 minutes at 3° C. This was then spun at 2,400 rpm for 10 minutes and the supernatant decanted and pooled.

The pool was cooled to 0° C. on ice and then 50.7 ml ethanol containing 0.5% ammonium acetate at −10° C. was added. This was left for 30 minutes and then spun for 10 minutes at 2400 rpm.

The supernatant was discarded and the precipitate washed with 50 ml ice cold ethanol. The precipitate was then dried in a vacuum desiccator for one hour.

This was then reconstituted in water tested for anti-thrombin activity, protein content and then vialed and freeze dried; the resulting volume was 1.5 ml.

The protein was estimated at 19 mg/ml using absorbance at 280 nm.

Activity was estimated as 1000 anti-thrombin units (ATU)/ml using the thrombin/fibrinogen clotting assay. The specific activity was calculated at 52.6 ATU/mg protein.

EXAMPLE 2

Step 1 as in Example 1 was repeated, followed by Steps 2 and 3 as follows.

Step 2—Cation Exchange Chromatography

Raw anti-thrombin was reconstituted in 10 mM Ammonium Acetate-Acetic Acid pH 4.0 and filtered to remove insolubles.

A carboxymethyl cellulose gel, commercially available under the trade mark CM Sephadex C50, was preswollen in buffer (10 mM Ammonium Acetate-Acetic Acid; pH 4.0) and packed into a 30 cm long column of 2.6 cm diameter. The sample was loaded onto the column.

100 ml buffer was run through the column and collected as waste. The buffer was then altered to 10 mM Ammonium Acetate pH 4.2. 10 ml fractions were then collected and tested for anti-thrombin activity and protein content. The specific activity for each fraction was calculated and fractions over a threshold value of specific activity were pooled, frozen and freeze dried.

Step 3—Anion-Exchange Chromatography

Figure 2:
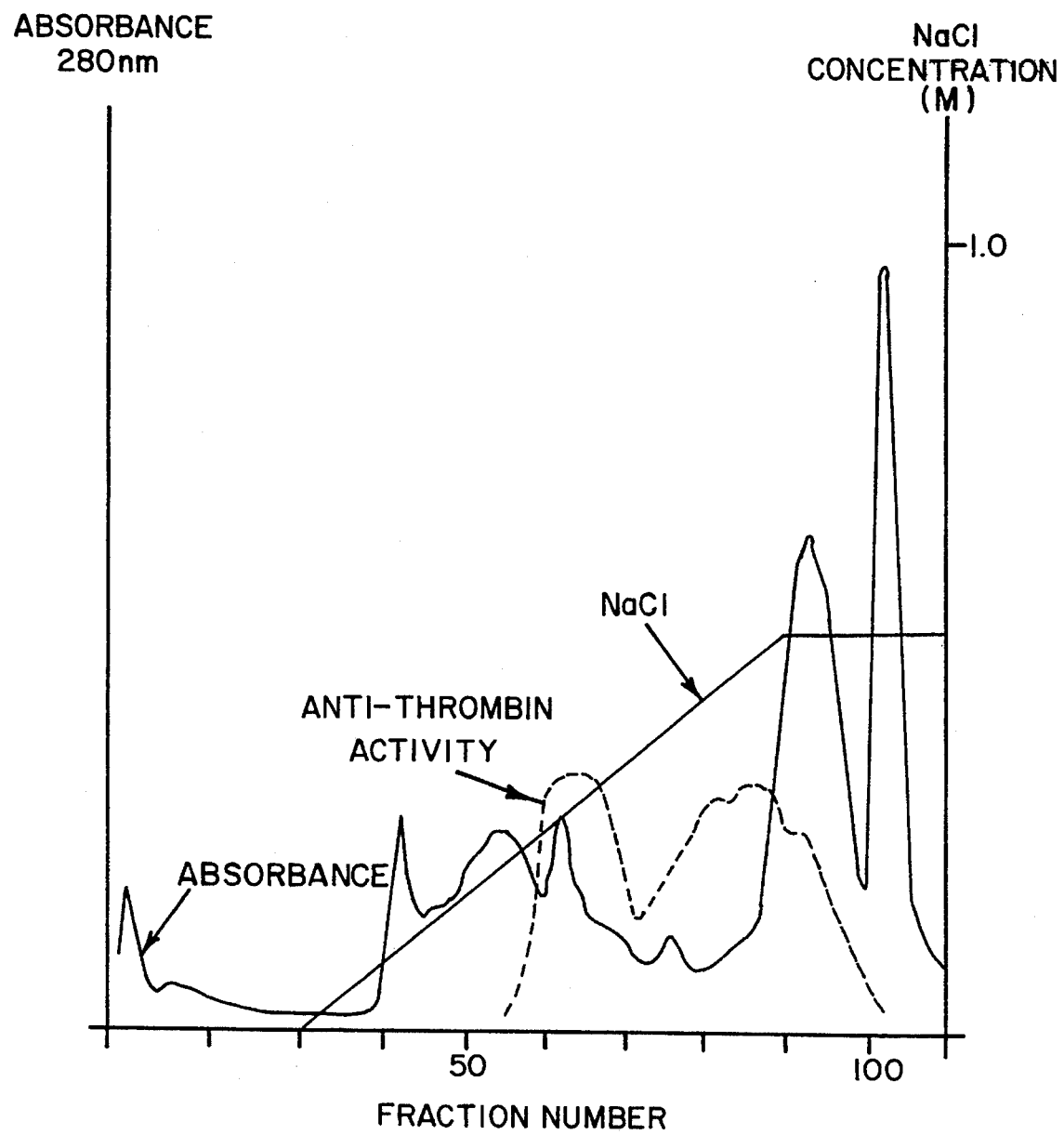
FIG. 2 is a chromatograph of post-CM Sephadex leach extract separated on DEAE Sephadex A25.

Lyophilised crude extract, produced either with ethanol extraction or CM Sephadex extraction, was reconstituted with 10 mM Tris/HCl buffer, pH 7.5 and chromatographed on a DEAE-Sephadex A-25 column (0.9×7 cm), pre-equilibrated with the same buffer. The column was developed at a flow rate of 15 ml/hr until the absorbance of the effluent at 234 nm was below 0.15. The bound material was then eluted with a linear gradient of 0–1M NaCl in the equilibration buffer (60 ml in each reservoir). The effluent was collected in 2 ml fractions for measurement of absorbance and inhibitory activity. The elution profiles obtained are shown for ethanol extracted material (FIG. 1) and CM Sephadex extracted material (FIG. 2).

The fractions containing with anti-thrombin activity were pooled, concentrated and desalted on Sephadex G-25 before further purification. The partially purified sample was further fractionated by affinity chromatography on thrombin Sepharose. The column was washed with the equilibration buffer (0.1M Tris/HCl, pH 8.0) and the bound anti-thrombin eluted with 1M benzamidine. The eluted material was lyophilised and desalted as before. The material was then purified by high performance liquid chromatography. 50 microliters of concentrated sample was applied to a microbore RP-300 C-8 column (3×0.21 cm) pre-equilibrated with 0.1% TFA at room temperature. The bound material was eluted with a 0–100% linear gradient of 60% acetonitrile, containing 0.09% TFA, in 35 min at a flow rate of 0.25 ml/min.

Figure 3:
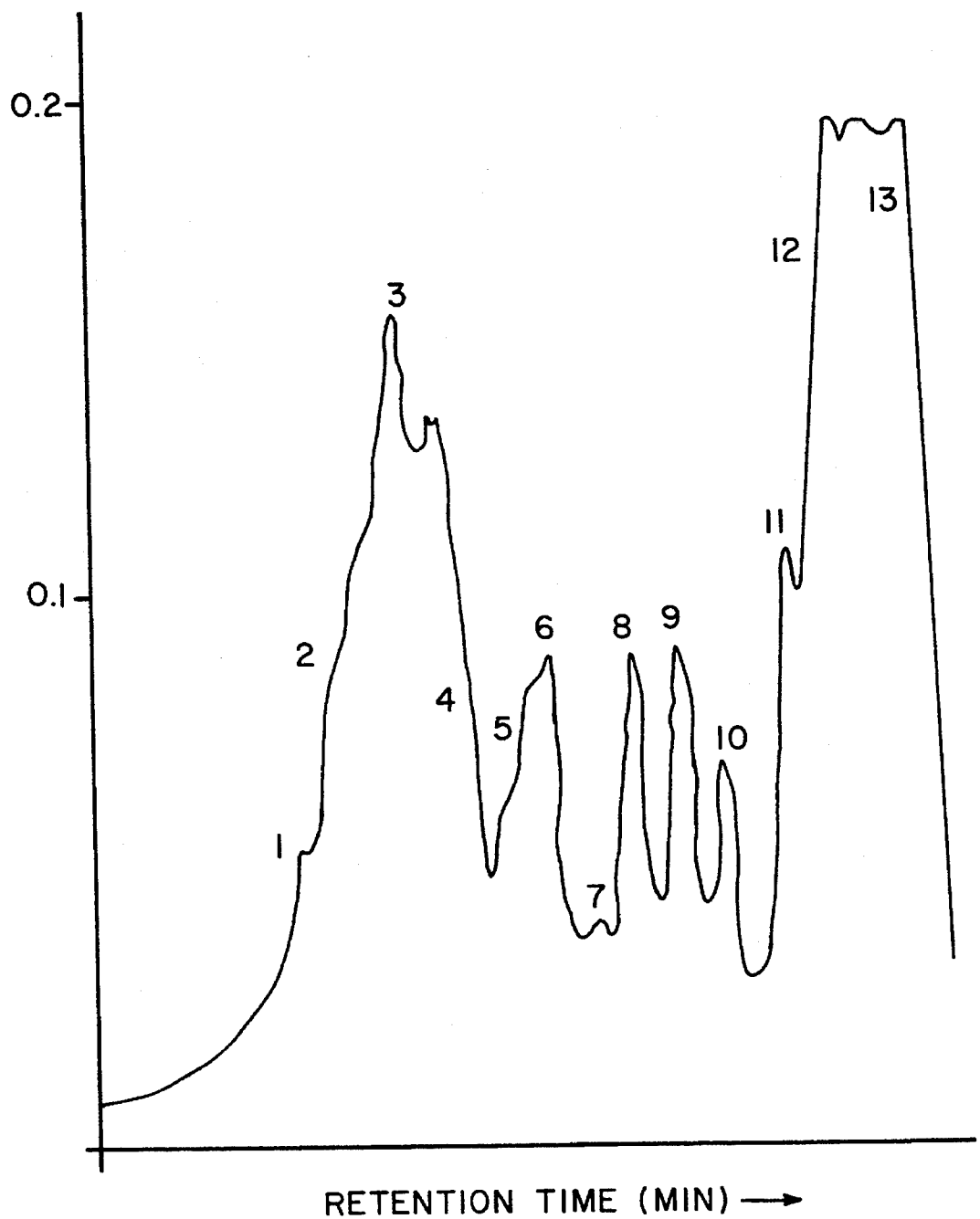
FIG. 3 is an HPLC profile of partially purified anti-thrombin.

The absorbance of the effluent was monitored at 215 nm. Each peak, or partially resolved peak, was collected as a separate fraction for measurement of its inhibitory activity. The elution profile obtained is shown in FIG. 3 and shows that the peaks containing anti-thrombin activity (peaks 5,6, 7) are separated from other peaks.

Sequencing

Major peaks containing anti-thrombin activity (equivalent to peaks 5,6 & 7 in FIG. 3) were dried under vacuum and analysed for N-terminal amino acid sequence on an automated Applied Biosystems gas phase sequencer (Model 470A) linked to an on-line analyser (Model 120) for identification of PTH amino acids.

Purified anti-thrombin sample was loaded directly onto the filter for sequencing. Cysteine residues in the sequence were determined after derivatisation to pyridylethyl cysteine by reaction of the purified sample with dithiothreitol and 4-vinylpyridine.

Tryptic digests of the reduced and pyridylethylated anti-thrombin were obtained with TPCK-trypsin. The reaction was carried out in 0.05M ammonium bicarbonate buffer at 37° C. for 4hr and the reaction stopped by freeze-drying and resuspension in 0.1% TFA. Fragments were separated by reversed phase HPLC under conditions similar to that described below in Example 3, step 5.

C-terminal sequencing was performed by combination of the carboxypeptidase Y digestion and DABS-Cl methods as described by Chang in FEBS letts (1983), 164 pp 307–313. The sequence thus determined was as given above.

EXAMPLE 3

Steps 1 and 2 as in Example 2 were repeated, followed by Steps 3 and 4 as follows:

Step 3. Anion Exchange Chromatography

Figure 4:
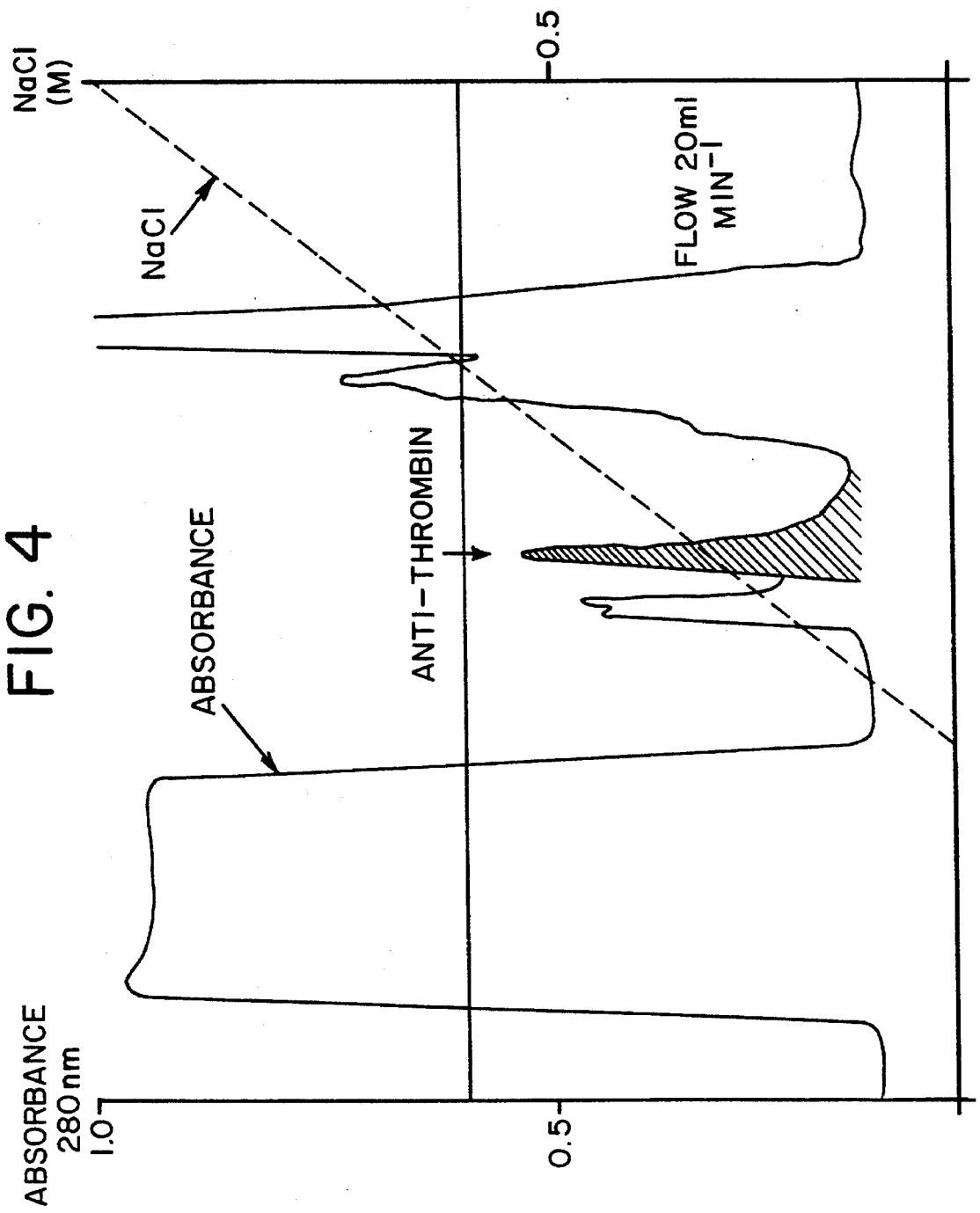
FIG. 4 is a anion exchange chromatograph of leech extract separated on Q Sepharose.

The solution from Step 2 was adjusted to pH 7.0 with 0.1M NaOH, and applied to a column containing an anion exchanger commercially available under the trade name Q-Sepharose, equilibrated in 20 mM Tris HCl, pH 7.0 buffer. Buffer was pumped through this column until unbound protein (detected by absorbance at 280 nm) was removed and then a gradient of salt (NACl in the same buffer) applied in a linear or stepwise manner to elute the bound anti-thrombin. A typical chromatographic profile is shown in FIG. 4.

Fractions containing anti-thrombin activity were pooled and concentrated by ultrafiltration to a volume of 25–50 ml. At this stage anti-thrombin preparations had a specific activity of 100–400 anti-thrombin units/mg protein.

Step 4. Gel Filtration

Figure 5:
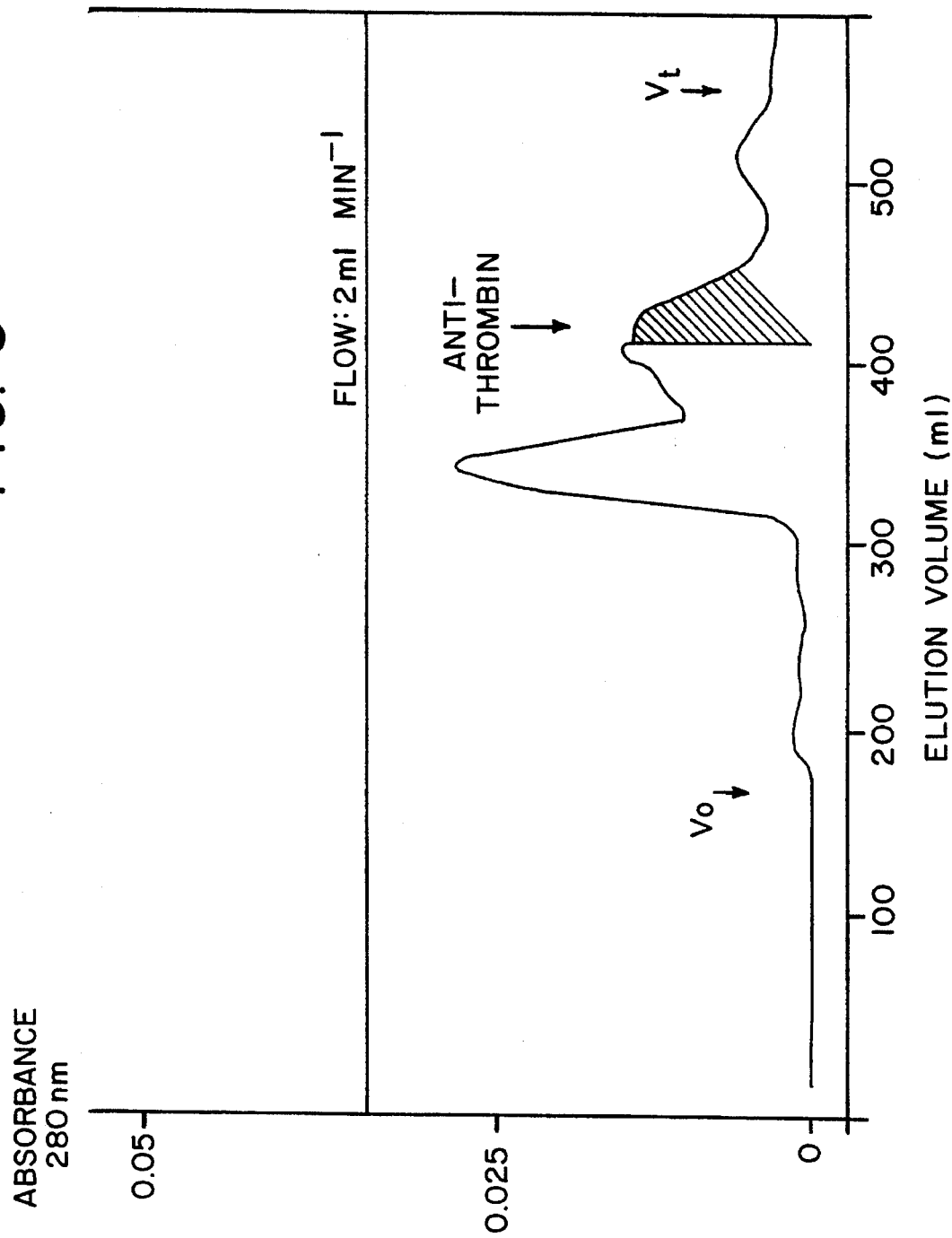
FIG. 5 is a graphic representation of the gel filtration of leech extract separated on Superdex 200.

The solution from Step 3 was applied to a gel filtration column commercially available as Superdex 200 equilibrated and eluted with 50 mM Tris HCl, 0.1M NaCl, pH 7.5. A typical chromatographic profile is shown in FIG. 5.

Fractions containing anti-thrombin activity were collected, pooled and lyophilised. At this stage, anti-thrombin preparations typically had a specific activity in the range of 1000–4000 anti-thrombin units/mg protein.

Step 5. Final Purification

Material from Step 4 was applied to an affinity column of thrombin-Sepharose equilibrated in 0.1M Trig HCl, pH 8.0 and the unbound material eluted with the same buffer. The bound anti-thrombin was eluted from the column with 1M benzamidine, lyophilised and then desalted using a column of Sephadex G25.

Figure 6:
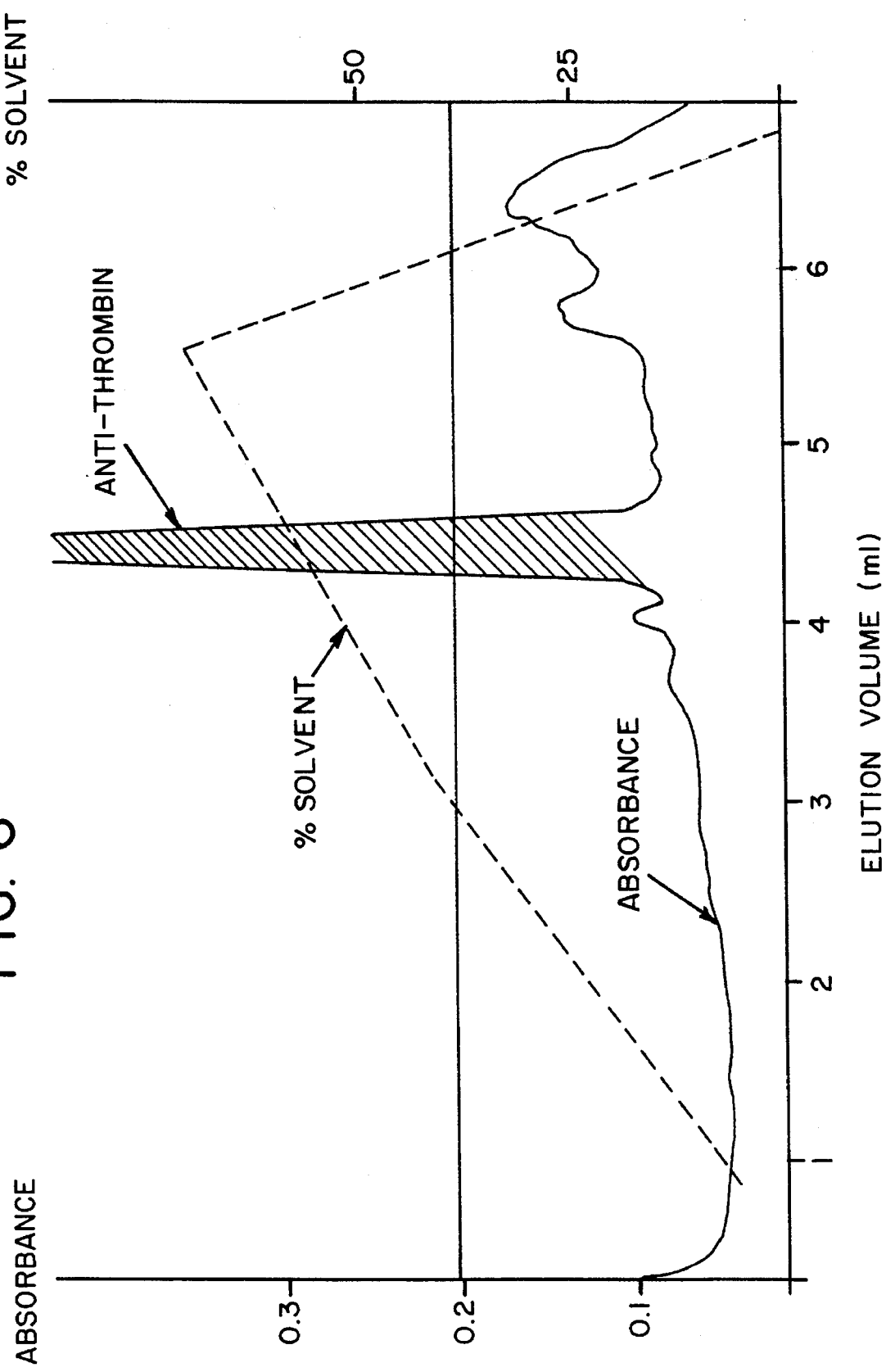
FIG. 6 is a reverse phase HPLC profile of affinity purified anti-thrombin.

Material purified by affinity chromatography was further purified by HPLC (high performance liquid chromatography) using a reverse-phase column (RP-300 C-8). In a typical example (FIG. 6), sample is applied to a column equilibrated in 0.1% trifluoroacetic acid (TFA) at room temperature and the bound anti-thrombin eluted with a linear gradient of 60% acetonitrile containing 0.9% TFA. Peaks of protein (detected by absorbance at 215/280nm) are collected and those containing anti-thrombin dried under vacuum.

Assay of Anti-thrombin Activity

Antithrombin activity was determined by measuring the inhibitor of the clotting activity of thrombin upon fibrinogen essentially as described by Markwardt in Methods in Enzymology; XIX, pp924; "Hirudin as an inhibitor of Thrombin" (1970), or by measuring the inhibition of thrombin cleavage of specific para-nitrophenol derived chromogenic substrates such as S-238 (commercially available from Kabi).

The activity of the anti-thrombin according to the invention was not neutralised by a high concentration of neutralising monoclonal antibodies specific for hirudin (this is further immunological confirmation that the anti-thrombin according to the invention and hirudin are dissimilar).

The anti-thrombin according to the invention and hirudin do however, have similar partial thromboplastic times for equivalent doses. This suggests that they have similar anti-coagulant properties towards human blood.

We claim:

1. A polypeptide having the following amino acid sequence, SEQ ID NO:4:

Xaa Xaa Tyr Thr Asp Cys Thr Glu Ser Gly Gln Asn Tyr Cys Leu
1           5                   10                      15

Cys Val Gly Ser Asn Val Cys Gly Glu Gly Asp Asn Cys Asn Xaa
                20                      25

Gln Leu Ser Ser Ser Gly Asn Gln Cys Val Xaa Gly Glu Gly Thr
30              35                  40

Pro Xaa Pro Gln Ser Gln Thr Glu Gly Asp Phe Glu Glu Ile Pro
45          50                  55                  60

Asp Glu Xaa Ile Lys
            65 wherein Xaa at positions 1, 2 and 63 is an amino acid residue; Xaa at position 30 is Cys or Pro; Xaa at position 41 is Glu, Asp or His; and Xaa at position 47 is Asp, Lys or Trp.

2. A polypeptide according to claim 1, wherein Xaa at position 1 is Val, SEQ ID NO:5.

3. A polypeptide according to claim 1, wherein Xaa at position 2 is Ser, SEQ ID NO:6.

4. A polypeptide according to claim 1, wherein Xaa at position 63 is Tyr, Tyr-SO$_3$H or a salt thereof, SEQ ID NO:7.

5. A polypeptide according to claim 1, wherein Xaa at position 1 is Val and Xaa at position 2 is Ser, SEQ ID NO:8.

6. A polypeptide according to claim 1, wherein Xaa at position 1 is Val and Xaa at position 63 is Tyr, Tyr-SO$_3$H or a salt thereof, SEQ ID NO:9.

7. A polypeptide according to claim 1, wherein Xaa at position 2 is Ser and Xaa at position 63 is Tyr, Tyr-SO$_3$H or a salt thereof, SEQ ID NO:10.

8. A polypeptide according to claim 1, wherein Xaa at position 1 represents Val; Xaa at position 2 is Ser; and Xaa at position 63 is Tyr, Tyr-SO$_3$H or a salt thereof, SEQ ID NO:11.

9. A pharmaceutical formulation which comprises a polypeptide according to claim 1 and a pharmaceutically acceptable carrier or excipient therefor.

10. A medicament for treatment of thromboembolic processes which comprises a polypeptide according to claim 1.

11. A medicament for according to claim 10, further comprising a plasminogen activator.

12. A polypeptide which specifically inhibits thrombin and which comprises the amino acid sequence:

Gly Asp Phe Glu Glu Ile Pro Asp Glu Xaa Ile Lys
1               5                   10 wherein Xaa represents an amino acid residue, SEQ ID NO:12.

13. A polypeptide according to claim 12, wherein Xaa is Tyr, Tyr-SO$_3$H or a salt thereof, SEQ ID NO:13.

14. A pharmaceutical formulation which comprises a polypeptide according to claim 12 and a pharmaceutically acceptable carrier or excipient therefor.

15. A polypeptide according to claim 12, wherein said polypeptide is derived from tissue or secretions of leeches of the species *Hirudinaria manillensis* by a process comprising the steps of:

(a) extracting said polypeptide with an organic solvent to form an extract, (b) isolating said polypeptide from said extract by ion exchange chromatography.

16. A composition comprising the polypeptide according to claim 12 and a plasminogen activator.

17. A polypeptide according to claim 1, wherein said polypeptide is derived from tissue or secretions or leeches of the species *Hirudinaria manillensis*.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65
        ( D ) OTHER INFORMATION: /product="OTHER"
            / note="Xaa at position 63 represent Tyr-SO3H."

( x ) PUBLICATION INFORMATION:
        ( A ) AUTHORS: Dodt, et al.,
        ( B ) TITLE: The Completed Amino Acid Sequence of Hirodin,
            A Thrombo- Specific Inhibitor
        ( C ) JOURNAL: FEBS Lett.
        ( D ) VOLUME: 165
        ( F ) PAGES: 180-184
        ( G ) DATE: 1984

( x i ) SEQUENCE DESCRIPTION: SEQ ID NO:1:

```
Val Val Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
                35                  40                  45

Gln Ser His Asn Asp Gly Asp Phe Glu Glu Ile Pro Glu Glu Xaa Leu
            50                  55                  60

Gln
65
```

( 2 ) INFORMATION FOR SEQ ID NO:2:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65
        ( D ) OTHER INFORMATION: /product="OTHER"
            / note="Xaa at position 63 represent Tyr-SO3H."

( x ) PUBLICATION INFORMATION:
        ( A ) AUTHORS: Dodt, et al.,
        ( B ) TITLE: Isolation and Characterization of Hirudin
            Isoinhibitors and Sequence Analysis of Hirudin PA
        ( C ) JOURNAL: Biol. Chem. Hoppe- Seyler
        ( D ) VOLUME: 367
        ( F ) PAGES: 803-811
        ( G ) DATE: 1986

( x i ) SEQUENCE DESCRIPTION: SEQ ID NO:2:

| Ile | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Lys | Gly | Asn | Lys | Cys | Ile | Leu | Gly | Ser |
|---|---|---|---|---|---|---|---|---|---|---|---|---|---|---|---|
| | | | 20 | | | | 25 | | | | | | 30 | | |

| Asn | Gly | Lys | Gly | Asn | Gln | Cys | Val | Thr | Gly | Glu | Gly | Thr | Pro | Asn | Pro |
|---|---|---|---|---|---|---|---|---|---|---|---|---|---|---|---|
| | | 35 | | | | | 40 | | | | | 45 | | | |

| Glu | Ser | His | Asn | Asn | Gly | Asp | Phe | Glu | Glu | Ile | Pro | Glu | Glu | Xaa | Leu |
|---|---|---|---|---|---|---|---|---|---|---|---|---|---|---|---|
| | 50 | | | | | 55 | | | | | 60 | | | | |

Gln
65

( 2 ) INFORMATION FOR SEQ ID NO:3:

( i ) SEQUENCE CHARACTERISTICS:
( A ) LENGTH: 65 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..65
( D ) OTHER INFORMATION: /product="OTHER"
/ note="Xaa at position 63 represent Tyr-SO3H."

( x ) PUBLICATION INFORMATION:
( A ) AUTHORS: Harvey et al.,
( B ) TITLE: Cloning and Expression of CDNA coding for the
Anti- Coagulant Hirudin From the Bloodsucking
Leech, Hirudo Medicinalis
( C ) JOURNAL: Proc. Natl. Acad. Sci. U.S.A.
( F ) PAGES: 1084-1088
( G ) DATE: 1986

( x i ) SEQUENCE DESCRIPTION: SEQ ID NO:3:

| Ile | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |

| Glu | Gly | Ser | Asn | Val | Cys | Gly | Lys | Gly | Asn | Lys | Cys | Ile | Leu | Gly | Ser |
|---|---|---|---|---|---|---|---|---|---|---|---|---|---|---|---|
| | | | 20 | | | | 25 | | | | | | 30 | | |

| Gln | Gly | Lys | Asp | Asn | Gln | Cys | Val | Thr | Gly | Glu | Gly | Thr | Pro | Lys | Pro |
|---|---|---|---|---|---|---|---|---|---|---|---|---|---|---|---|
| | | 35 | | | | | 40 | | | | | 45 | | | |

| Gln | Ser | His | Asn | Gln | Gly | Asp | Phe | Glu | Pro | Ile | Pro | Glu | Asp | Xaa | Asp |
|---|---|---|---|---|---|---|---|---|---|---|---|---|---|---|---|
| | 50 | | | | | 55 | | | | | 60 | | | | |

Glu
65

( 2 ) INFORMATION FOR SEQ ID NO:4:

( i ) SEQUENCE CHARACTERISTICS:
( A ) LENGTH: 65 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..65
( D ) OTHER INFORMATION: /product="OTHER"
/ note="Xaa at positions 1, 2 and 63 represent an amino acid;
Xaa at position 30 represent Cys or Pro; Xaa at position 41
represent Glu, Asp or His; and Xaa at position 47 represent
Asp, Trp or Lys."

( x i ) SEQUENCE DESCRIPTION: SEQ ID NO:4:

| Xaa | Xaa | Tyr | Thr | Asp | Cys | Thr | Glu | Ser | Gly | Gln | Asn | Tyr | Cys | Leu | Cys |
| 1 | | | | 5 | | | | | 10 | | | | | 15 | |

| Val | Gly | Ser | Asn | Val | Cys | Gly | Glu | Gly | Asp | Asn | Cys | Asn | Xaa | Gln | Leu |
| | | | 20 | | | | | 25 | | | | | 30 | | |

| Ser | Ser | Ser | Gly | Asn | Gln | Cys | Val | Xaa | Gly | Glu | Gly | Thr | Pro | Xaa | Pro |
| | | 35 | | | | | 40 | | | | | 45 | | | |

| Gln | Ser | Gln | Thr | Glu | Gly | Asp | Phe | Glu | Glu | Ile | Pro | Asp | Glu | Xaa | Ile |
| | 50 | | | | | 55 | | | | | 60 | | | | |

Lys
65

( 2 ) INFORMATION FOR SEQ ID NO:5:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65
        ( D ) OTHER INFORMATION: /product="OTHER"
/ note="Xaa at position 2 and Xaa at position 63 represent an
amino acid; Xaa at position 41 represent Glu, Asp or His; and
Xaa at position 47 represent Asp, Lys or Trp."

( x i ) SEQUENCE DESCRIPTION: SEQ ID NO:5:

| Val | Xaa | Tyr | Thr | Asp | Cys | Thr | Glu | Ser | Gly | Gln | Asn | Tyr | Cys | Leu | Cys |
| 1 | | | | 5 | | | | | 10 | | | | | 15 | |

| Val | Gly | Ser | Asn | Val | Cys | Gly | Glu | Gly | Asp | Asn | Cys | Asn | Xaa | Gln | Leu |
| | | | 20 | | | | | 25 | | | | | 30 | | |

| Ser | Ser | Ser | Gly | Asn | Gln | Cys | Val | Xaa | Gly | Glu | Gly | Thr | Pro | Xaa | Pro |
| | | 35 | | | | | 40 | | | | | 45 | | | |

| Gln | Ser | Gln | Thr | Glu | Gly | Asp | Phe | Glu | Glu | Ile | Pro | Asp | Glu | Xaa | Ile |
| | 50 | | | | | 55 | | | | | 60 | | | | |

Lys
65

( 2 ) INFORMATION FOR SEQ ID NO:6:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65
        ( D ) OTHER INFORMATION: /product="OTHER"
/ note="Xaa at position 1 and Xaa at position 63 represent an
amino acid; Xaa at position 30 represent Cys or Pro; Xaa at
position 41 represent Glu, Asp or His; and Xaa at position 47
represent Asp, Lys or Trp."

( x i ) SEQUENCE DESCRIPTION: SEQ ID NO:6:

| Xaa | Ser | Tyr | Thr | Asp | Cys | Thr | Glu | Ser | Gly | Gln | Asn | Tyr | Cys | Leu | Cys |
| 1 | | | | 5 | | | | | 10 | | | | | 15 | |

```
Val  Gly  Ser  Asn  Val  Cys  Gly  Glu  Gly  Asp  Asn  Cys  Asn  Xaa  Gln  Leu
               20                       25                      30

Ser  Ser  Ser  Gly  Asn  Gln  Cys  Val  Xaa  Gly  Glu  Gly  Thr  Pro  Xaa  Pro
               35                       40                      45

Gln  Ser  Gln  Thr  Glu  Gly  Asp  Phe  Glu  Glu  Ile  Pro  Asp  Glu  Xaa  Ile
          50                       55                      60

Lys
65
```

( 2 ) INFORMATION FOR SEQ ID NO:7:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65
        ( D ) OTHER INFORMATION: /product="OTHER"
    / note="Xaa at positions 1 and 2 represent an amino acid; Xaa
    at position 30 represent Cys or Pro; Xaa at position 41
    represent Glu, Asp or His; Xaa at position 47 represent Asp,
    Trp or Lys; and Xaa at position 63 is Tyr, Tyr-SO3H, or a salt
    thereof."

( x i ) SEQUENCE DESCRIPTION: SEQ ID NO:7:

```
Xaa  Xaa  Tyr  Thr  Asp  Cys  Thr  Glu  Ser  Gly  Gln  Asn  Tyr  Cys  Leu  Cys
1                   5                        10                      15

Val  Gly  Ser  Asn  Val  Cys  Gly  Glu  Gly  Asp  Asn  Cys  Asn  Xaa  Gln  Leu
               20                       25                      30

Ser  Ser  Ser  Gly  Asn  Gln  Cys  Val  Xaa  Gly  Glu  Gly  Thr  Pro  Xaa  Pro
               35                       40                      45

Gln  Ser  Gln  Thr  Glu  Gly  Asp  Phe  Glu  Glu  Ile  Pro  Asp  Glu  Xaa  Ile
          50                       55                      60

Lys
65
```

( 2 ) INFORMATION FOR SEQ ID NO:8:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..65
        ( D ) OTHER INFORMATION: /product="OTHER"
    / note="Xaa at position 30 represent Cys or Pro; Xaa at
    position 41 represent Glu, Asp or His; Xaa at position 47
    represent Asp, Trp or Lys; and Xaa at position 63 represent an
    amino acid."

( x i ) SEQUENCE DESCRIPTION: SEQ ID NO:8:

```
Val  Ser  Tyr  Thr  Asp  Cys  Thr  Glu  Ser  Gly  Gln  Asn  Tyr  Cys  Leu  Cys
1                   5                        10                      15

Val  Gly  Ser  Asn  Val  Cys  Gly  Glu  Gly  Asp  Asn  Cys  Asn  Xaa  Gln  Leu
               20                       25                      30

Ser  Ser  Ser  Gly  Asn  Gln  Cys  Val  Xaa  Gly  Glu  Gly  Thr  Pro  Xaa  Pro
```

-continued

```
                      35                          40                        45
        Gln  Ser  Gln  Thr  Glu  Gly  Asp  Phe  Glu  Glu  Ile  Pro  Asp  Glu  Xaa  Ile
             50                        55                        60

Lys
        65
```

(2) INFORMATION FOR SEQ ID NO:9:

(i) SEQUENCE CHARACTERISTICS:
 (A) LENGTH: 65 amino acids
 (B) TYPE: amino acid
 (C) STRANDEDNESS: single
 (D) TOPOLOGY: linear (ii) MOLECULE TYPE: protein (ix) FEATURE:
 (A) NAME/KEY: Protein
 (B) LOCATION: 1..65
 (D) OTHER INFORMATION: /product="OTHER"
/ note="Xaa at position 2 represent an amino acid; Xaa at
position 30 represent Cys or Pro; Xaa at position 41 represent
Glu, Asp or His; Xaa at position 47 represent Asp, Trp or Lys;
Xaa at position 63 is Tyr, Tyr-SO3H, or a salt thereof."

(xi) SEQUENCE DESCRIPTION: SEQ ID NO:9:

```
        Val  Xaa  Tyr  Thr  Asp  Cys  Thr  Glu  Ser  Gly  Gln  Asn  Tyr  Cys  Leu  Cys
        1                   5                        10                       15

Val  Gly  Ser  Asn  Val  Cys  Gly  Glu  Gly  Asp  Asn  Cys  Asn  Xaa  Gln  Leu
                       20                       25                       30

Ser  Ser  Ser  Gly  Asn  Gln  Cys  Val  Xaa  Gly  Glu  Gly  Thr  Pro  Xaa  Pro
                  35                        40                       45

Gln  Ser  Gln  Thr  Glu  Gly  Asp  Phe  Glu  Glu  Ile  Pro  Asp  Glu  Xaa  Ile
             50                       55                        60

Lys
        65
```

(2) INFORMATION FOR SEQ ID NO:10:

(i) SEQUENCE CHARACTERISTICS:
 (A) LENGTH: 65 amino acids
 (B) TYPE: amino acid
 (C) STRANDEDNESS: single
 (D) TOPOLOGY: linear (ii) MOLECULE TYPE: protein (ix) FEATURE:
 (A) NAME/KEY: Protein
 (B) LOCATION: 1..65
 (D) OTHER INFORMATION: /product="OTHER"
/ note="Xaa at position 1 is an amino acid; Xaa at position 30
represent Cys or Pro; Xaa at position 41 represent Glu, Asp,
or His; Xaa at position 47 represent Asp, Trp or Lys; Xaa at
position 63 is Tyr, Tyr-SO3H, or a salt thereof."

(xi) SEQUENCE DESCRIPTION: SEQ ID NO:10:

```
        Xaa  Ser  Tyr  Thr  Asp  Cys  Thr  Glu  Ser  Gly  Gln  Asn  Tyr  Cys  Leu  Cys
        1                   5                        10                       15

Val  Gly  Ser  Asn  Val  Cys  Gly  Glu  Gly  Asp  Asn  Cys  Asn  Xaa  Gln  Leu
                       20                       25                       30

Ser  Ser  Ser  Gly  Asn  Gln  Cys  Val  Xaa  Gly  Glu  Gly  Thr  Pro  Xaa  Pro
                  35                        40                       45

Gln  Ser  Gln  Thr  Glu  Gly  Asp  Phe  Glu  Glu  Ile  Pro  Asp  Glu  Xaa  Ile
             50                       55                        60
```

Lys
65

( 2 ) INFORMATION FOR SEQ ID NO:11:

( i ) SEQUENCE CHARACTERISTICS:
( A ) LENGTH: 65 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..65
( D ) OTHER INFORMATION: /product="OTHER"
/ note="Xaa at position 30 represent Cys or Pro; Xaa at
position 41 represent Glu, Asp or His; Xaa at position 47
represent Asp, Trp or Lys; and Xaa at position 63 represent
Tyr, Tyr-SO3H or a salt thereof."

( x i ) SEQUENCE DESCRIPTION: SEQ ID NO:11:

Val  Ser  Tyr  Thr  Asp  Cys  Thr  Glu  Ser  Gly  Gln  Asn  Tyr  Cys  Leu  Cys
1                   5                        10                       15

Val  Gly  Ser  Asn  Val  Cys  Gly  Glu  Gly  Asp  Asn  Cys  Asn  Xaa  Gln  Leu
               20                       25                       30

Ser  Ser  Ser  Gly  Asn  Gln  Cys  Val  Xaa  Gly  Glu  Gly  Thr  Pro  Xaa  Pro
          35                       40                       45

Gln  Ser  Gln  Thr  Glu  Gly  Asp  Phe  Glu  Glu  Ile  Pro  Asp  Glu  Xaa  Ile
     50                       55                       60

Lys
65

( 2 ) INFORMATION FOR SEQ ID NO:12:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..12
( D ) OTHER INFORMATION: /product="OTHER"
/ note="Xaa at position 10 represent an amino acid."

( x i ) SEQUENCE DESCRIPTION: SEQ ID NO:12:

Gly  Asp  Phe  Glu  Glu  Ile  Pro  Asp  Glu  Xaa  Ile  Lys
1                   5                        10

( 2 ) INFORMATION FOR SEQ ID NO:13:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..12
( D ) OTHER INFORMATION: /product="OTHER"
/ note="Xaa at position 10 represent Tyr, Tyr-SO3H or a salt
thereof."

(xi) SEQUENCE DESCRIPTION: SEQ ID NO:13:

Gly Asp Phe Glu Glu Ile Pro Asp Glu Xaa Ile Lys
1               5                       10